US00PP34569P2

(12) United States Plant Patent
Graff

(10) Patent No.: US PP34,569 P2
(45) Date of Patent: Sep. 13, 2022

(54) ***HIBISCUS* PLANT NAMED 'HQ301'**

(50) Latin Name: *Hibiscus rosa-sinensis*
Varietal Denomination: HQ301

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 17/694,017

(22) Filed: Mar. 14, 2022

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
See application file for complete search history.

*Primary Examiner* — Annette H Para
(74) *Attorney, Agent, or Firm* — C. Anne Whealy

(57) ABSTRACT

A new and distinct cultivar of *Hibiscus* plant named 'HQ301', characterized by its upright, mounding, dense and bushy plant habit; moderately vigorous growth habit; dark green-colored leaves; uniform and freely flowering habit; large vivid red-colored flowers with dark purple-colored throats; and good flower longevity.

1 Drawing Sheet

Botanical designation: *Hibiscus rosa-sinensis.*
Cultivar denomination: 'HQ301'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Graff Breeding A/S of Sabro, Denmark on Nov. 26, 2021, application number 2021/3051. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hibiscus* plant, botanically known as *Hibiscus rosa-sinensis*, and hereinafter referred to by the name 'HQ301'.

The new *Hibiscus* plant is a product of a planned breeding program conducted by the Inventor in Sabro, Denmark The objective of the breeding program is to create new strong *Hibiscus* plants with attractive and long-lasting flowers.

The new *Hibiscus* plant originated from a cross-pollination in August, 2016 in Sabro, Denmark of a proprietary selection of *Hibiscus rosa-sinensis* identified as code designation HQ-1230, not patented, as the female, or seed, parent with a proprietary selection of *Hibiscus rosa-sinensis* identified as code designation HQ-0031, not patented, as the male, or pollen, parent. The new *Hibiscus* plant was discovered and selected by the Inventor as a flowering plant within the progeny of the stated cross-pollination in a controlled greenhouse environment in Sabro, Denmark in May, 2017.

Asexual reproduction of the new *Hibiscus* plant by vegetative terminal cuttings in a controlled greenhouse environment in Sabro, Denmark since September, 2019 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HQ301'. These characteristics in combination distinguish 'HQ301' as anew and distinct *Hibiscus* plant:

1. Upright, mounding, dense and bushy plant habit.
2. Moderately vigorous growth habit.
3. Dark green-colored leaves.
4. Uniform and freely flowering habit.
5. Large vivid red-colored flowers with dark purple-colored throats.
6. Good flower longevity.

Plants of the new *Hibiscus* can be compared to plants of the female parent selection. Plants of the new *Hibiscus* differ primarily from plants of the female parent selection in flower longevity as flowers of plants of the new *Hibiscus* last about two to three days whereas flowers of plants of the female parent selection last about one to two days.

Plants of the new *Hibiscus* can be compared to plants of the male parent selection. Plants of the new *Hibiscus* differ primarily from plants of the male parent selection in the following characteristics:

1. Plants of the new *Hibiscus* are larger than plants of the male parent selection.
2. Plants of the new *Hibiscus* have larger flowers than plants of the male parent selection.

Plants of the new *Hibiscus* can be compared to plants of the *Hibiscus rosa-sinensis* 'Adonis', disclosed in U.S. Plant Pat. No. 21,592. In side-by-side comparisons, plants of the new *Hibiscus* differ from plants of 'Adonis' in the following characteristics:

1. Plants of the new *Hibiscus* have broader and glossier leaves than plants of 'Adonis'.
2. Flowers of plants of the new *Hibiscus* are red in color whereas flowers of plants of 'Adonis' have dark pink-colored flowers.
3. Plants of the new *Hibiscus* have smaller sepals than plants of 'Adonis'.

BRIEF DESCRIPTION OF THE PHOTOGRAPH

The accompanying colored photograph illustrates the overall appearance of the new *Hibiscus* plant showing the colors as true as it is reasonably possible to obtain in colored reproductions of this type. Colors in the photograph may differ slightly from the color values cited in the detailed botanical description which accurately describe the colors of the new *Hibiscus* plant. The photograph is a side perspective view of a typical flowering plant of 'HQ301' grown in a container.

DETAILED BOTANICAL DESCRIPTION

The aforementioned photograph and following observations, measurements and values describe plants grown during the spring in 23-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time about eight weeks after planting and plants were 26 weeks old when the photograph and the description were taken. In the description, color references are made to The Royal Horticultural Society Colour Chart, 2001 Edition, except where general terms of ordinary dictionary significance are used.

Botanical classification: *Hibiscus rosa-sinensis* 'HQ301'.

Parentage:

*Female, or seed, parent.*—Proprietary selection of *Hibiscus rosa-sinensis* identified as code number HQ-1230, not patented.

*Male or pollen parent.*—Proprietary selection of *Hibiscus rosa-sinensis* identified as code number HQ-0031, not patented.

Propagation:

*Type.*—By vegetative terminal cuttings.

*Time to initiate roots, summer.*—About three weeks at ambient and soil temperatures about 24° C.

*Time to initiate roots, winter.*—About four weeks at ambient and soil temperatures about 24° C.

*Time to produce a rooted young plant, summer.*—About eight weeks at ambient and soil temperatures about 24° C.

*Time to produce a rooted young plant, winter.*—About nine weeks at ambient and soil temperatures about 24° C.

*Root description.*—Medium in thickness, fleshy; color, close to 158A, actual color of the roots is dependent on substrate composition, water quality, fertilizer type and formulation, substrate temperature and physiological age of roots.

*Rooting habit.*—Freely branching; dense.

Plant description:

*Plant and growth habit.*—Container plant; upright, mounding, and bushy and dense plant habit; moderately vigorous growth habit.

*Branching habit.*—Freely branching habit with lateral branches potentially forming at every node; pinching enhances lateral branch development.

*Plant height, soil level to top of floral plane.*—About 35 cm to 55 cm.

*Plant diameter* (*area of spread*).—About 30 cm to 50 cm.

Lateral branch description:

*Length.*—About 12 cm to 20 cm.

*Diameter.*—About 5 mm to 7 mm.

*Internode length.*—About 1 cm to 3 cm.

*Strength.*—Strong.

*Texture.*—Smooth, glabrous; becoming woody with development.

*Color.*—Close to 165A; when woody, color becoming closer to 195A.

Leaf description:

*Arrangement.*—Alternate, single; numerous.

*Length.*—About 8 cm to 11 cm.

*Width.*—About 8 cm to 11 cm.

*Shape.*—Cordate.

*Apex.*—Acute.

*Base.*—Cordate.

*Margin.*—Crenate.

*Texture and luster, upper surface.*—Smooth, glabrous; glossy.

*Texture and luster, lower surface.*—Scattered pubescence; venation prominent; slightly glossy.

*Venation pattern.*—Pinnate; arcuate.

*Color.*—Developing leaves, upper surface: Close to 137A. Developing leaves, lower surface: Close to 138A. Fully expanded leaves, upper surface: Close to N189A; venation, close to 137A. Fully expanded leaves, lower surface: Close to 137A; venation, close to 137A.

*Petioles.*—Length: About 2 cm to 4 cm. Diameter: About 3 mm. Texture, upper and lower surfaces: Sparsely pubescent. Color, upper surface: Close to N200A. Color, lower surface: Close to N199A.

*Leaf stipules.*—Quantity and arrangement: Two at the base of the petiole, opposite. Length: About 1 cm. Diameter: About 2 mm. Shape: Linear to lanceolate. Color, upper and lower surfaces: Distally, close to 138A and proximally, close to N200A.

Flower description:

*Flower arrangement.*—Single-type flowers borne at terminal leaf axils; uniform, continuous and freely flowering habit with numerous flowers developing per plant; flowers face mostly upright to slightly outwardly.

*Fragrance.*—None detected.

*Natural flowering season.*—Plants flower in the garden during the spring and summer or during periods of warm weather; in the greenhouse, plants can be flowered year-round; plants begin flowering about 12 to 16 weeks after pinching.

*Flower longevity*.—Good flower longevity, flowers last for about three days; flowers persistent.

*Flower diameter*.—About 18 cm to 20 cm.

*Flower length* (*height*).—About 10 cm to 12 cm.

*Flower throat diameter*.—About 3 cm to 5 cm.

*Flower buds*.—Rate of opening: Flowers buds open in about three days. Length: About 4 cm to 6 cm. Diameter: About 2 cm to 3 cm. Shape: Ovate to lanceolate. Color: Close to 59A.

*Petals*.—Arrangement: Five petals in a single whorl; petals imbricate. Length: About 9 cm to 10 cm. Width: About 9 cm to 11 cm. Shape: Roughly spatulate to fan-shaped. Apex: Rounded. Base: Attenuate. Margin: Entire; moderately flared and undulate. Texture and luster, upper surface: Glabrous; rough with a velvety appearance; matte. Texture and luster, lower surface: Glabrous, rough with a satiny appearance; slightly glossy. Color: When opening and fully opened, upper surface: Close to 45A; venation, close to N77A; color does not change with subsequent development. When opening and fully opened, lower surface: Close to 47A; venation, close to 46A; color does not change with subsequent development. Throat: Close to N77A.

*Sepals*.—Appearance: Five sepals fused into a campanulate-shaped calyx. Length: About 2 cm. Width: About 1 cm. Shape: Lanceolate. Apex: Acuminate. Margin: Entire. Texture, upper surface: Rough, glabrous. Texture, lower surface: Smooth, glabrous. Color, upper surface: Close to 137A. Color, lower surface: Close to 138A.

*Peduncles*.—Length: About 4 cm to 5 cm. Diameter: About 3 mm to 5 mm. Strength: Strong. Aspect: Mostly upright. Texture: Sparsely pubescent. Color: Close to N200A and 137A.

*Reproductive organs*.—Androecium: Stamen number: Numerous, more than 100. Filament length: About 5 mm to 10 mm. Filament color: Close to 46A. Anther length: About 1 mm to 2 mm. Anther shape: Reniform. Anther color: Close to 22A. Amount of pollen: Abundant. Pollen color: Close to 17A. Gynoecium: Pistil length: About 10 cm to 11 cm. Staminal column texture: Smooth, waxy. Staminal column color: Close to 46A; towards the base, close to N77A. Style length: About 10 cm to 11 cm; five-parted at the apex. Style color: Close to 155A. Stigma appearance: Five rounded stigma pads. Stigma pad color: Close to 59A. Ovary color: Close to 157A.

*Seeds and fruits*.—To date, seed and fruit development has not been observed on plants of the new *Hibiscus*.

Temperature tolerance: Plants of the new *Hibiscus* have been observed to have tolerate temperatures from about 10° C. to about 40° C.

Pathogen & pest resistance: To date, plants of the new *Hibiscus* not been observed to be resistant to pathogens and pests common to *Hibiscus* plants.

It is claimed:

1. A new and distinct *Hibiscus* plant named 'HQ301' as illustrated and described.

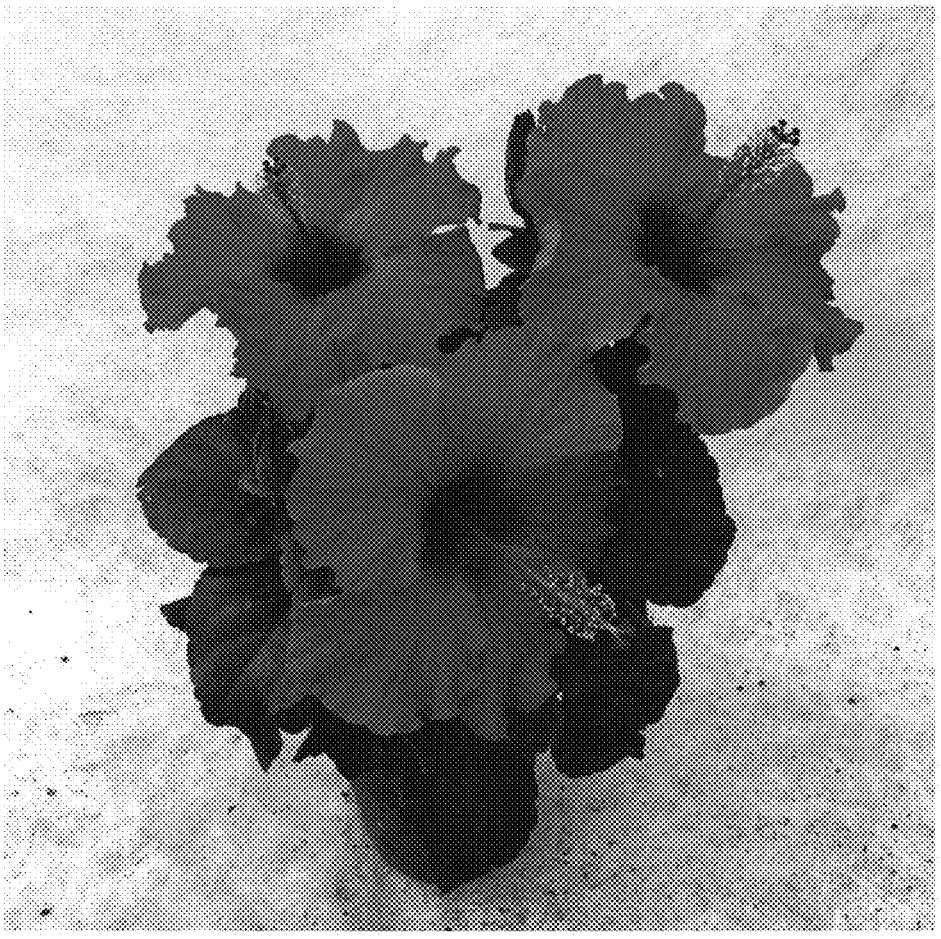

* * * * *